United States Patent [19]
Kawada et al.

[11] Patent Number: 6,027,926
[45] Date of Patent: Feb. 22, 2000

[54] METHOD OF PRODUCING OPTICALLY ACTIVE 1,2,4-BUTANETRIOL

[75] Inventors: Naoki Kawada, Ibaraki; Rika Kinase, Chiba, both of Japan

[73] Assignee: Daicel Chemical Industries, Ltd., Sakai, Japan

[21] Appl. No.: 09/078,461

[22] Filed: May 14, 1998

[30] Foreign Application Priority Data

May 14, 1997 [JP] Japan .................................. 9-123998

[51] Int. Cl.$^7$ .................................. C12P 7/18; C12N 1/14
[52] U.S. Cl. ........................... 435/158; 435/171; 435/280
[58] Field of Search ..................................... 435/158, 280, 435/171

[56] References Cited

FOREIGN PATENT DOCUMENTS 6-209781  8/1994  Japan .

OTHER PUBLICATIONS

Chemical Abstracts, vol. 121, No. 21, Nov. 21, 1994, Columbus, Ohio, US; abstract No. 253903g, Nikaido, Teruyuki, et al., "Manufacture of optically active alcohols with Pseudomonas."

*Primary Examiner*—Herbert J. Lilling
*Attorney, Agent, or Firm*—Fish & Richardson P.C.

[57] ABSTRACT

Optically active 1,2,4-butanetriol of high optical purity can be produced economically and simply using a microorganism capable of increasing the content of (S)-1,2,4-butanetriol or (R)-1,2,4-butanetriol by acting on a mixture of enantiomers of 1,2,4-butanetriol.

16 Claims, No Drawings

METHOD OF PRODUCING OPTICALLY ACTIVE 1,2,4-BUTANETRIOL

FIELD OF THE INVENTION

The present invention relates to a method of producing optically active 1,2,4-butanetriol.

BACKGROUND OF THE INVENTION

Optically active 1,2,4-butanetriol is an important starting material for synthesis of various medicaments (for example, antiviral agents). The known methods for production of optically active 1,2,4-butanetriol that have been conventionally used include the method of preparing it by reducing (S)- or (R)-malic acid ester (for example, Tandon et al., J. Org. Chem. 40, 2767 (1983)) and the method of synthesizing (R)-1,2,4-butanetriol from L-erythritol (Van der Eycken et al., Tetrahedron Lett. 28, 4759, (1987)). However, these methods are economically disadvantageous in that they require expensive catalysts.

The known methods utilizing microorganisms include the method of allowing (R)-1,2,4-butanetriol to remain from a mixture of enantiomers of 1,2,4-butanetriol by using a microorganism belonging to the genus Pseudomonas (Japanese Laid-open Publication No. Hei 6-209781). However, the method has a drawback in that the concentration of the product is low.

There has been no report on the method of production of (S)-1,2,4-butanetriol from a mixture of enantiomers of 1,2,4-butanetriol by utilizing a microorganism.

SUMMARY OF THE INVENTION

An object of the present invention is to provide an economically advantageous and simple method for production of optically active 1,2,4-butanetriol of high optical purity.

The present inventors paid attention to the use of microorganisms for the method of economically and simply producing optically active 1,2,4-butanetriol of high optical purity and screened microorganisms that could achieve this object. As a result, the present inventors found that the content of (S)-1,2,4-butanetriol in the reaction mixture was markedly increased when certain specific microorganisms were allowed to act on a mixture of enantiomers of 1,2,4-butanetriol and that the content of (R)-1,2,4-butanetriol in the reaction mixture was increased when specific microorganisms were allowed to act on a mixture of enantiomers of 1,2,4-butanetriol. Furthermore, it was found that optically active 1,2,4-butanetriol of high optical purity could be obtained economically and simply by using such microorganisms and, thus, the present invention was completed.

The present invention relates to:

(1) a method of producing (S)-1,2,4-butanetriol, which comprises contacting a microorganism or treated product thereof, which is capable of increasing the content of (S)-1,2,4-butanetriol by acting on a mixture of enantiomers of 1,2,4-butanetriol, with the mixture of enantiomers of 1,2,4-butanetriol to increase the content of (S)-1,2,4-butanetriol. Preferably, (2) the method as described in (1) above, wherein the microorganism belongs to the genus selected from the group consisting of Bacillus, Candida, Comamonas, Cryptococcus, Dekkera, Eremascus, Hansenula, Klebsiella, Schizoblastosporion, Stephanoascus, and Sterigmatomyces. More preferably, (3) the method as described in (1) above, wherein the microorganism belongs to the species selected from the group consisting of *Bacillus subtilis, Candida succiphila, Comamonas acidovorans, Cryptococcus curiosus, Cryptococcus humicolus, Cryptococcus neoformans, Dekkera custersianus, Eremascus fertilis, Hansenula glucozyma, Hansenula polymorpha, Schizoblastosporion kobayasii, Stephanoascus ciferii*, and *Sterigmatomyces elviae*, and *Sterigmatomyces polyborus*.

The present invention also relates to:

(4) a method of producing (R)-1,2,4-butanetriol, which comprises contacting a microorganism or treated product thereof, which is capable of increasing the content of (R)-1,2,4-butanetriol by acting on a mixture of enantiomers of 1,2,4-butanetriol, with the mixture of enantiomers of 1,2,4-butanetriol to increase the content of (R)-1,2,4-butanetriol. Preferably, (5) the method as described in (4) above, wherein said microorganism belongs to the genus selected from the group consisting of Geotrichum, Sterigmatomyces, Trichosporon, and Yarrowia. More preferably, (6) the method as described in (4) above, wherein said microorganism belongs to the species selected from the group consisting of *Geotrichum candidum, Geotrichum fermentans, Sterigmatomyces halophilus, Trichosporon cutaneum*, and *Yarrowia lipolytica*.

DETAILED DESCRIPTION OF THE INVENTION

The microorganisms to be used in the present invention are not particularly restricted as far as they are capable of increasing the content of (S)-1,2,4-butanetriol by acting on a mixture of enantiomers of 1,2,4-butanetriol or to increase the content of (R)-1,2,4-butanetriol by acting on a mixture of enantiomers of 1,2,4-butanetriol.

The microorganisms capable of increasing the content of (S)-1,2,4-butanetriol include, for example, those belonging to the genus Bacillus, Candida, Comamonas, Cryptococcus, Dekkera, Eremascus, Hansenula, Klebsiella, Schizoblastosporion, Stephanoascus, or Sterigmatomyces. Preferable examples thereof include those belonging to the species *Bacillus subtilis, Candida succiphila, Comamonas acidovorans, Cryptococcus curiosus, Cryptococcus humicolus, Cryptococcus neoformans, Dekkera custersianus, Eremascus fertilis, Hansenula glucozyma, Hansenula polymorpha, Schizoblastosporion kobayasii, Stephanoascus ciferii, Sterigmatomyces elviae*, or *Sterigmatomyces polyborus*, for example, Bacillus subtilis IFO 3007, Bacillus subtilis IFO 3037, Candida succiphila DSM 2149, Comamonas acidovorans IFO 13582, Cryptococcus curiosus IFO 1336, Crytcoccus humicolus IFO 0760, Cryptococcus neoformans IAM 4788, Dekkera custersianus IFO 1585, Eremascus fertilis IFO 0691, Hansenula glucozyma DSM 70271, Hansenula polymorpha ATCC 26012, Schizoblastosporion kobayasii IFO 1644, Stephanoascus ciferii IFO 1854, Sterigmatomyces elviae DSM 70852, Sterigmatomyces polyborus DSM 70853, and the like.

The microorganisms capable of increasing the content of (R)-1,2,4-butanetriol include, for example, those belonging to the genus Trichosporon, Yarrowia, Geotrichum, or Sterigmatomyces. Preferable examples thereof include those belonging to the species *Trichosporon cutaneum, Yarrowia lipolytica, Geotrichum Candidum, Geotrichum fermentans*, or *Sterigmatomyces halophilus*, for example, Trichosporon cutaneum IFO 0173, Yarrowia lipolytica IFO 1550, Geotrichum candidum IFO 31810, Geotrichum candidum IFO 4597, Geotrichum candidum IFO 4598, Geotrichum candidum IFO 5308, Geotrichum candidum JCM 1747, Geotrichum candidum JCM 5222, Geotrichum fermentans JCM 2467, and *Sterigmatomyces halophilus* IFO 1488. Any strain of these microorganisms, for example, wild strains, variants, and recombinant strains produced by genetic techniques such as cell fusion or gene manipulation can suitably be used.

The above microorganisms with IFO numbers are recited in the List of Cultures 10th edition (1996) published by the Institute of Fermentation, Osaka (IFO), and are available from IFO. The above microorganisms with ATCC numbers are recited in the Catalogue of Bacteria & Bacteriophages 18th edition (1992) published by the "American Type Culture Collection (ATCC)" and are available from the ATCC. The above microorganisms with JCM numbers are recited in the 6 th edition of the Catalogue of Microbial Strains (1995) published by the microbial strain preservation facilities of the Institute of Physical and Chemical Research and are available from the institute. The above microorganisms with DSM numbers are recited in the Catalogue of Strains (1989) published by "Deutsche Sammlung von Mikroorganismen und Zellkulturen GmbH (DSM)" and can be obtained from DSM. The microorganisms with IAM numbers are recited in the first edition of Catalogue of Strains of Microorganisms Microalgae, the Institute of Applied Microbiology, University of Tokyo (1993) published by the Association for Advancement of Applied Microbiological Research, and can be obtained from IAM.

The culture media to be used in the present invention are not particularly restricted as long as the microorganisms used in the present invention can grow therein. As carbon sources, for example, any compound can be used as far as the above microorganisms can use them. Specific examples thereof include sugars such as glucose, fructose, sucrose, or dextrin, alcohols such as sorbitol, ethanol, or glycerol, organic acids such as fumaric acid, citric acid, acetic acid, or propionic acid or their salts, hydrocarbons such as paraffin, or mixtures of these compounds. Examples of nitrogen sources include ammonium salts of inorganic acid, such as ammonium chloride, ammonium sulfate, or ammonium phosphate, ammonium salts of organic acids, such as ammonium fumarate, or ammonium citrate, inorganic or organic nitrogen-containing substances such as meat extract, yeast extract, corn steep liquor, hydrolysate of casein, or urea, or mixtures of these substances. Nutrients used for ordinary cultures such as inorganic salts, trace mineral salts, and vitamins can also be added. If required, factors that promote the growth of the microorganisms, factors that increase the capability of producing the desired compounds of the present invention, or materials effective for maintaining pH of the culture media may also be added.

Cultivation can be carried out either anaerobically or aerobically under the conditions suitable for the growth of the microorganisms, for example, that the pH of the culture medium is usually 3–9, preferably 4–8, and the temperature is usually 20–45° C., preferably 25–37° C. The period of cultivation is usually 5–120 hours, preferably 12–72 hours.

The reaction can be effected by the method comprising adding a mixture of enantiomers of 1,2,4-butanetriol to the culture medium as it is recovered, or the method comprising separating the microbial cells by centrifugation or the like and resuspending the cells as they are or after washing in a buffer or water and adding a mixture of enantiomers of 1,2,4-butanetriol to the suspension. It is sometimes preferable to add carbon sources such as glucose or sucrose as energy sources upon the reaction. The microbial cells can be used as either in the living form or in the form of their treated products such as disrupted cells, acetone-treated products, lyophilized products, or the like. These microbial cells or their treated products may be immobilized by the known methods such as polyacrylamide gel method, sulfur-containing polysaccharide gel method (carageenan method), alginic acid gel method, agar gel method, and the like. Further, it is possible to use enzymes obtained by purifying from treated microbial cells using known methods.

The mixture of enantiomers of 1,2,4-butanetriol may be added as such or dissolved in water or an organic solvent that does not affect the reaction and then added to the reaction mixture. It may also be dispersed in a surfactant or the like. The mixture of enantiomers of 1,2,4-butanetriol may be added all at once from the beginning of the reaction or added in divided portions.

The reaction is conducted at usually pH 3–10, preferably pH 5–9, at a temperature of usually 10–30° C., preferably 20–40° C., with stirring or at a static state. The reaction time is usually about 1 to about 120 hours. As the reaction time is prolonged, optically active 1,2,4-butanetriol of high optical purity can be obtained though the remaining amount of 1,2,4-butanetriol is decreased. The concentration of the substrate used is not particularly restricted, but about 0.1 w/v % to about 10 w/v % based on the reaction mixture is usually preferable.

The optically active 1,2,4-butanetriol that is formed by the reaction can be easily collected directly from the reaction mixture before or after the microbial cells have been separated from the reaction mixture. The optically active 1,2,4-butanetriol can be collected using ordinary purification methods such as extraction with organic solvents, distillation, column chromatography, or the like.

The present invention provided a method of producing optically active 1,2,4-butanetriol utilizing microorganisms. According to the production method of the present invention, it is possible to simply and easily produce optically active 1,2,4-butanetriol of high optical purity, which give remarkable advantage in the industrial production.

The present invention will be described with reference to the following Examples, but is not construed to be limited to these Examples. In Examples, 1,2,4-butanetriol in the reaction mixture was easily determined by gas chromatography. The optical purity was determined by acetylating optically active 1,2,4-butanetriol obtained by the reaction with acetyl chloride by the ordinary method and subjecting it to high performance liquid chromatography using an optical resolution column (chiralcel OB 25 cm×4.6 mm φ (Daicel Chemical Industries, Ltd.), mobile phase: hexane/isopropanol=19/1, flow rate: 1 ml/min., detection: 220 nm, column temperature: 40° C.).

EXAMPLE 1

A 5 ml portion of the culture medium for preparation of microbial cells (glucose 20 g/l, polypeptone 5 g/l, yeast extract 3 g/l, and malt extract 3 g/l (pH 6.0)) was poured in a test tube having a diameter of 21 mm. After sterilization, microorganisms shown in Table 1 were respectively inoculated and cultured at 30° C. for 24 hours under shaking. The microbial cells were separated by centrifugation to obtain living microbial cells. Then, a 5 ml portion of an aqueous solution containing 50 mg of racemates of 1,2,4-butanetriol and 50 mg of $CaCO_3$ was poured in a test tube having a diameter of 21 mm. The living microbial cells obtained above were suspended in this solution and the reaction was allowed to proceed at 30° C. for 60 hours under reciprocating shaking. After completion of the reaction, the microbial cells were removed by centrifugation. The supernatant thus obtained was dehydrated to obtain syrup, which was acetylated with acetyl chloride by the ordinary method. The resulting product was dissolved in a solvent and subjected to high performance liquid chromatography to determine the absolute configuration and optical purity of 1,2,4-butanetriol thus obtained. The results are shown in table 1.

TABLE 1

| Strain | Absolute Configuration | Optical purity of 1,2,4-butanetriol (% ee) |
| --- | --- | --- |
| Bacillus subtilis IFO 3007 | S | 11.5 |
| Bacillus subtilis IFO 3037 | S | 10.5 |
| Candida succiphila DSM 2149 | S | 11.6 |
| Comamonas acidovorans IFO 13582 | S | 15.1 |
| Cryptococcus curiosus IFO 1336 | S | 33.8 |
| Cryptococcus humicolus IFO 0760 | S | 96.2 |
| Cryptococcus neoformans IAM 4788 | S | 15.7 |
| Dekkera custersianus IFO 1585 | S | 12.1 |
| Eremascus fertilis IFO 0691 | S | 19.2 |
| Hansenula glucozyma DSM 70271 | S | 10.2 |
| Hansenula polymorpha ATCC 26012 | S | 45.8 |
| Schizoblastosporion kabayashii IFO 1644 | S | 21.9 |
| Stephanoascus ciferii IFO 1854 | S | 35.1 |
| Sterigmatomyces elviae DSM 70852 | S | 10.9 |
| Sterigmatomyces polyborus DSM 70853 | S | 51.1 |
| Geotrichum candidum IFO 31810 | R | 11.8 |
| Geotrichum candidum IFO 4597 | R | 45.3 |
| Geotrichum candidum IFO 4598 | R | 74.4 |
| Geotrichum candidum IFO 5368 | R | 11.3 |
| Geotrichum candidum JCM 1747 | R | 64.4 |
| Geotrichum candidum JCM 8222 | R | 78.0 |
| Geotrichum fermentans JCM 2467 | R | 10.4 |
| Sterigmatomyces halophilu IFO 1488 | R | 13.5 |
| Trichosporon cutaneum IFO 0173 | R | 27.8 |
| Yarrowia lipolytica IFO 1550 | R | 16.7 |

EXAMPLE 2

Cryptococcus humicolus IFO 0760, Cryptococcus curiosus IFO 1336, Sterigmatomyces elviae DSM 70852, and Sterigmatomyces polyborus DSM 70853 were respectively inoculated in 50 ml of the culture medium for preparation of microbial cells as in Example 1 contained in a 500-ml ribbed flask and cultured for at 30° C. for 24 hours under shaking. After completion of the culturing, 15 ml of the culture was collected by centrifugation and suspended in 5 ml of an aqueous solution prepared by adding 100 mg of racemates of 1,2,4-butanetriol and 50 mg of CaCO$_3$ to distilled water. The reaction was allowed to proceed at 30° C. for 60 hours under reciprocating shaking. After completion of the reaction, microbial cells were removed by centrifugation and the resulting supernatant was subjected to gas chromatography to determine the content of 1,2,4-butanetriol. Then, the supernatant was removed to obtain syrup which was acetylated with acetyl chloride by the ordinary method, dissolved in a solvent, and subjected to high performance liquid chromatography to determine the absolute configuration and optical purity of 1,2,4-butanetriol thus obtained. The results are shown in Table 2.

TABLE 2

| Strain | Concentration of remaining 1,2,4-butanetriol (g/L) | Absolute configuration | Optical purity of 1,2,4-butanetriol (% ee) |
| --- | --- | --- | --- |
| Cryptococcus humicola IFO 0760 | 12.0 | S | 55 |
| Cryptococcus curiasus IFO 1336 | 7.7 | S | 67 |
| Sterigmatomyces elviae DSM 70852 | 10.8 | S | 96 |
| Sterigmatamyces polyborus DSM 70853 | 14.2 | S | 51 |

EXAMPLE 3

Sterigmatomyces elviae DSM 70852 was inoculated to two 1-liter jar fermentors containing 600 ml of the culture medium for preparation of microbial cells as in Example 1. The inoculated medium was cultured at 30° C., at 600 rpm and aeration of 1 vvm for 20 hours under shaking. After completion of the culturing, the microbial cells was collected by centrifugation and suspended in 400 ml of an aqueous solution containing 6 g of racemates of 1,2,4-butanetriol and 4 g of CaCO$_3$. The reaction was allowed to proceed in a 1-liter jar fermentor at 30° C. at 800 rpm and aeration of 1 vvm for 52 hours under shaking. After completion of the reaction, the microbial cells were removed by centrifugation and the resulting supernatant was subjected to gas chromatography to determine the content of 1,2,4-butanetriol. Then, the supernatant was distilled off to obtain syrup, which was acetylated with acetyl chloride, dissolved in a solvent, and subjected to high performance liquid chromatography to determine the absolute configuration and optical purity of the thus-obtained 1,2,4-butanetriol. As a result, 3.9 g of (S)-1,2,4-butanetriol having optical purity of 94.5% ee was obtained.

What is claimed is:

1. A method of producing (S)-1,2,4-butanetriol comprising contacting (a) a mixture of enantiomers of 1,2,4-butanetriol with (b) a microorganism or a disrupted, acetone-treated, or lyophilized microorganism, wherein the microorganism increases the relative amount of (S)-1,2,4-butanetriol in the mixture.

2. The method of claim 1 wherein the microorganism belongs to a genus selected from the group consisting of Bacillus, Candida, Comamonas, Cryptococcus, Dekkera, Eremascus, Hansenula, Klebsiella, Schizoblastosporion, Stephanoascus, and Sterigmatomyces.

3. The method of claim 1 wherein the microorganism belongs to a species selected from the group consisting of Bacillus subtilis, Candida succiphila, Comamonas acidovorans, Cryptococcus curiosus, Cryptococcus humicolus, Cryptococcus neoformans, Dekkera custersianus, Eremascus fertilis, Hansenula glucozyma, Hansenula polymorpha, Schizoblastosporion kobayashii, Stephanoascus ciferii, Sterigmatomyces elviae, and Sterigmatomyces polyborus.

4. The method of claim 1 wherein the microorganism is of a strain selected from the group consisting of Bacillus subtilis IFO 3007, Bacillus subtilis IFO 3037, Candida succiphila DSM 2149, Comamonas acidovorans IFO 13582, Cryptococcus curiosus IFO 1336, Cryptococcus humicolus IFO 0760, Cryptococcus neoformans IAM 4788, Dekkera custersianus IFO 1585, Eremascus fertilis IFO 0691, Hansenula glucozyma DSM 70271, Hansenula polymorpha ATCC 26021, Schizoblastosporion kobayasii IFO 1644, Stephanoascus ciferii IFO 1854, Sterigmatomyces elviae DSM 70852, and Sterigmatomyces polyborus DSM 70853.

5. The method of claim 1 wherein the microorganism is a recombinant microorganism.

6. The method of claim 2 wherein the microorganism is a recombinant microorganism.

7. The method of claim 1 wherein the microorganism or disrupted, acetone-treated, or lyophilized microorganism is immobilized on a solid substrate prior to the contacting step.

8. The method of claim 1 wherein the microorganism or disrupted, acetone-treated, or lyophilized microorganism is suspended in an aqueous solution prior to the contacting step.

9. The method of claim 1 wherein the contacting step comprises incubating the microorganism or disrupted, acetone-treated, or lyophilized microorganism with the mixture of enantiomers of 1,2,4-butanetriol for at least 1 hour.

10. A method of producing (R)-1,2,4-butanetriol comprising contacting (a) a mixture of enantiomers of 1,2,4-butanetriol with (b) a microorganism or a disrupted, acetone-treated, or lyophilized microorganism, wherein the microorganism belongs to a genus selected from the group consisting of Geotrichum, Sterigmatomyces, Trichosporon, and Yarrowia, and wherein the microorganism increases the content of (R)-1,2,4-butanetriol in the mixture.

11. The method of claim 10, wherein the microorganism belongs to a species selected from the group consisting of Geotrichum Candidum, *Geotrichum fermentans, Sterigmatomyces halophilus, Trichosporon cutaneum*, and *Yarrowia lipolytica*.

12. The method of claim 10, wherein the microorganism is of a strain selected from the group consisting of *Trichosporon cutaneum* IFO 0173, *Yarrowia lipolytica* IFO 1550, Geotrichum Candidum IFO 31810, Geotrichum Candidum IFO 4597, Geotrichum Candidum IFO 4598, Geotrichum Candidum IFO 5308, Geotrichum Candidum JCM 1747, Geotrichum Candidum JCM 5222, *Geotrichum fermentans* JCM 2467, and *Sterigmatomyces halophilus* IFO 1488.

13. The method of claim 10 wherein the microorganism is a recombinant microorganism.

14. The method of claim 10 wherein the microorganism or disrupted, acetone-treated, or lyophilized microorganism is immobilized on a solid substrate prior to the contacting step.

15. The method of claim 10 wherein the microorganism or disrupted, acetone-treated, or lyophilized microorganism is suspended in an aqueous solution prior to the contacting step.

16. The method of claim 10 wherein the contacting step comprises incubating the microorganism or disrupted, acetone-treated, or lyophilized microorganism with the mixture of enantiomers of 1,2,4-butanetriol for at least 1 hour.

* * * * *